United States Patent [19]
Tulin-Silver et al.

[11] Patent Number: 5,508,282
[45] Date of Patent: Apr. 16, 1996

[54] COMPOSITION AND METHOD FOR TREATING ACUTE OR CHRONIC RHINOSINUSITIS

[75] Inventors: Jeffrey Tulin-Silver, 2818 Parkridge, Ann Arbor, Mich. 48103; William H. Pearson, Ann Arbor, Mich.

[73] Assignee: Jeffrey Tulin-Silver, Ann Arbor, Mich.

[21] Appl. No.: 61,548

[22] Filed: May 17, 1993

[51] Int. Cl.$^6$ ............................ A61K 31/52; A61K 31/34
[52] U.S. Cl. .............................................. 514/264; 514/474
[58] Field of Search ................................... 514/264, 474, 514/849

[56] References Cited

U.S. PATENT DOCUMENTS

| | | | |
|---|---|---|---|
| 3,856,942 | 12/1974 | Murphy | 514/474 |
| 4,061,797 | 12/1977 | Hannan et al. | 426/590 |
| 4,410,556 | 10/1983 | Lunder et al. | 426/597 |
| 4,525,341 | 6/1985 | Deihl | 514/474 |
| 4,826,683 | 5/1989 | Bates | 424/641 |
| 4,940,728 | 7/1990 | Postley | 514/474 |

OTHER PUBLICATIONS

Andersen et al "Vitamin C & The Common Cold: a Double Blend Trul"; CMA Journal vol. 107 Sep. 23, 1972 pp. 502–508.
Geber et al 83 CA: 72008v 1975.
Merck Index 18th Ed Cit. #'s 846, 1093, 1606 & 3487 (1989).

Primary Examiner—Raymond Henley, III
Attorney, Agent, or Firm—Alex Rhodes

[57] ABSTRACT

A stable, non-irritating composition and method for treating, without side effects, acute or chronic rhinosinusitis and its associated upper airway symptoms. The composition and treatment are useful for relieving the symptoms, and shortening the duration, of acute or chronic rhinosinusitis. The composition comprises a therapeutically effective solution having a pH of about 6.0, of ascorbic acid and caffeine, in combination with other soluble vitamins, natural ingredients and preservatives in a pharmaceutically acceptable carrier. The method includes the steps of preparing and administering the composition to the nasal membranes of a patient in the form of a nasal spray or drops.

22 Claims, No Drawings

COMPOSITION AND METHOD FOR TREATING ACUTE OR CHRONIC RHINOSINUSITIS

FIELD OF THE INVENTION

The present invention generally relates to a composition and method for relieving and shortening the duration of inflamed nasal membrane turbinates (which include allergic, infectious, vasomotor, atrophic, hormonally-induced vasomotor instability and non-allergic causes); nasal and sinus congestion (such as that in sinus headaches associated with acute or chronic sinusitis); and additionally, inflammation and congestion of the eustachian tube (Eustachian Tube Dysfunction), collectively referred to herein as "rhinitis" or "rhinosinusitis."

BACKGROUND OF THE INVENTION

Virtually all persons are occasionally stricken with acute upper respiratory infections (common colds), acute or chronic allergy flare-ups of the nose, and/or acute or chronic non-allergic rhinosinusitis. Significant discomfort and inconvenience are usually incurred by persons afflicted by such conditions. All of these disorders are characterized by intense inflammation of the nasal membranes (nasal turbinates). A number of symptoms which, at least in part, contribute to the discomfort and inconvenience associated with the common cold or other rhinosinusitis symptoms often include one or more of the following: nasal congestion, post-nasal drip, decreased sense of smell, ear fullness, headache, sore throat, malaise, muscle and joint aches, fatigue, cough, chest congestion, fever, chills and gastrointestinal maladies. Considerable research has been conducted over the years aimed at reducing the incidence and duration of symptoms associated with allergies and common colds, and at suppressing or eliminating their accompanying symptoms.

Current medications and treatments for rhinosinusitus provide only minimal symptom relief and some have undesirable side effects. Over-the-counter medications containing antihistamines sometimes cause drowsiness and impair cognitive judgment so that driving an automobile or operating other power driven machinery can be dangerous. Decongestants and adrenalin derivatives can elevate blood pressure, cause heart palpitations and stimulate brain activity causing insomnia or hyperalertness.

Over-the-counter decongestant sprays relieve some rhinosinusitis symptoms, but are associated with significant addictive, rebound phenomenon of the nasal membranes (Rhinitis Medicamentosa). As a result, over-the-counter decongestant sprays may actually lengthen the duration of common cold or rhinosinusitis symptoms.

Inhaled corticosteroid nasal sprays provide some relief for allergic rhinitis but do not reduce inflammation caused by acute viral infections, or inflammation associated with other forms of non-allergic rhinitis (atrophic rhinitis, vasomotor rhinitis, hormonally-induced vasomotor instability, etc.).

Vitamin compositions for treating disorders of the sino-nasal area do not have troubling side effects but heretofore have not shown a significant benefit in treating these disorders.

Several laboratory studies within the last two decades have shown that certain vitamins and other natural ingredients have anti-inflammatory properties. However, large scale clinical studies conducted in the 1980's using Vitamin C tablets showed that oral Vitamin C had no significant benefit in lessening the symptoms of the common cold.

Heretofore, aqueous solutions of ascorbic acid with a pH equal to or greater than 6.0 have been unstable and subject to quick oxidation by air. Solutions of ascorbic acid with a pH somewhat below 6.0 are undesirable because they tend to be irritating to some patients. Solutions with a pH equal to or greater than 6.0 have required precautions in preparation and use, by way of example, oxygen-free solvents, air tight packages, air tight misters, etc.

Applicants' studies have shown that to be therapeutically effective for treating rhinosinusitis, ascorbic acid must be applied to nasal membranes in higher concentration than heretofore used.

Applicants' studies have also shown that nasal spray solutions containing therapeutically effective amounts of ascorbic acid which have been prepared by methods other than Applicants' method have very short shelf lives because the ascorbic acid crystallizes out of solution.

Applicants' studies have also shown that nasal spray solutions containing ascorbic acid and caffeine in therapeutically effective amounts provide substantial benefits in treating acute and chronic rhinosinusitis.

Applicants' studies have also shown that nasal spray solutions containing ascorbic acid and caffeine at a pH of 6.5 do not require precautions in preparation and use, such as oxygen-free solvents, air-tight packages, air-tight misters, etc.

Deihl, J. A., U.S. Pat. No. 4,525,341 teaches a method for treating vitamin deficiency by spraying a solution containing small concentrations of vitamins and a breath freshening agent in an alcohol carrier into the nose or mouth.

Postley, J. E., U.S. Pat. No. 4,940,728 teaches a method for treating disorders of the sino-nasal area by spraying an alkaline solution (pH=7.8) containing small concentrations (13.3 mg/ml) of ascorbic acid and a salt or ester of ascorbic acid into the nasal mucous membrane.

Bates, H. L., U.S. Pat. No. 4,826,683 discloses a nasal spray for relieving nasal and sinus congestion consisting essentially of small concentrations of vitamin C, vegetable oil, and other vitamins and natural ingredients.

SUMMARY OF THE INVENTION

The present invention is an effective and easy to use composition and method for treating acute or chronic rhinitis or rhinosinusitis.

Another benefit of the present invention is that a nasal spray composition is provided for treating acute or chronic rhinosinusitis which is non-irritating and does not have undesirable side effects.

Another benefit of the present invention is that a nasal spray composition is provided having a therapeutically effective amount of Vitamin C which does not crystallize the Vitamin C out of solution.

Another benefit of the present invention is that nasal spray compositions containing Vitamin C at a pH of 5.5 to 6.5 do not require special precautions in their preparation and use, such as oxygen-free solvents, air-tight packages, air-tight misters, etc.

The therapeutically effective nasal spray composition is a mixture of caffeine and Vitamin C (ascorbic acid) dissolved in a pharmaceutically acceptable carrier, adjusted to a final pH of about 5.5 to about 6.5, and administered to the nasal membrane. The therapeutically effective composition is prepared from sodium ascorbate or ascorbic and with an adjustment of pH to the desired value with sodium hydroxide, sodium bicarbonate or sodium carbonate.

As used herein, by "therapeutically effective composition or solution" is meant a composition or solution which is effective for relieving the symptoms and shortening the duration of rhinitis or rhinosinusitus without side effects. By "pharmaceutically acceptable carrier" is meant any composition, solvent, dispersion medium, coating, delivery vehicle or the like, which can be employed to administer the compositions of the present invention without undue adverse physiological effects.

It is contemplated that additional water soluble vitamins and/or minerals will also be dissolved in the treatment solution (see Table I).

DETAILED DESCRIPTION OF THE PREFERRED EMBODIMENT

The present invention is a novel nasal spray composition and method for treating rhinosinusitus. Generally, the nasal spray composition is a stable, non-irritating mixture containing therapeutically effective amounts of Vitamin C, and caffeine, along with other water soluble vitamins, natural ingredients and preservatives. Vitamin C and caffeine, alone or in combination, in a pharmaceutically acceptable carrier, are important therapeutic ingredients in the formulation of the invention (see Table I).

By "pharmaceutically acceptable carrier" is meant a composition, solvent, dispersion medium, coating, delivery vehicle or the like, which can be employed to administer the compositions of the present invention without undue adverse physiological effects. Suitable pharmaceutically acceptable carriers used in preparing the nasal spray of the invention preferably include diluents such as normal saline or deionized water as well as benzoic acid or sodium benzoate, and disodium EDTA hydrate.

The therapeutically effective solution of the present invention is administered as a nasal spray via a metered-dose spray device or as nasal drops topically applied to the nasal membrane. By "therapeutically effective solution" is meant a solution which is generally effective to achieve the desired effects of relieving the symptoms and shortening the duration of rhinitis.

Preferred Nasal Spray Composition

Suitable ingredients, and contemplated concentrations, for use in the preferred nasal spray composition are presented in Table I and Table II. The compounds of Table I are preferred ingredients for use in the nasal spray formulation since they each exhibit one or more of the following characteristics: they help repair cell membranes; they are antioxidants (i.e. they remove cellular toxins or cellular waste material); they can stimulate the immune system; and they can improve the sense of smell. Caffeine, shown in Table II, is employed as a topical vasoconstrictor. The remaining ingredients shown in Table II are suitable for use in the carrier vehicle.

While the preferred amount of caffeine is 17 mg/ml, as shown in Table II, the contemplated range of caffeine concentration according to the present invention is about 5 to about 100 mg/ml.

It is to be noted that the preferred ingredients of the nasal spray composition include only water soluble vitamins and other natural compounds, so that all ingredients that are absorbed from the nasal mucous membranes will be readily excreted from the user's body within several hours without forming toxic metabolites.

The nasal spray solution is formulated to achieve a final pH of less than 6.5; more preferably, the pH falls within the desired range of about 5.5 to 6.5. In a most preferred embodiment of the invention, the nasal spray formulation comprises a solution containing ascorbic acid, caffeine, benzoic acid or sodium benzoate, and disodium EDTA hydrate within a pH limit of from about 5.5 to about 6.5.

TABLE I

| VITAMINS AND/OR MINERALS | AMOUNT (per solution) |
| --- | --- |
| VITAMIN C (ASCORBIC ACID)* | 15–300 mg |
| PANTOTHENIC ACID | 30–100 mg |
| VITAMIN B-6 (PYRIDOXINE) | 20–100 mg |
| VITAMIN B-2 (RIBOFLAVIN) | 10–50 mg |
| VITAMIN B-1 (THIAMINE) | 30–150 mg |
| VITAMIN B-12 (CYANOCOBALAMIN) | 100–500 mcg |
| FOLIC ACID | 0.4–5 mg |
| ZINC | 0.50 mg |
| SELENIUM | 5–20 mcg |

*or an equivalent concentration of sodium ascorbate

TABLE II

| OTHER INGREDIENTS | AMOUNT (per mL solution) |
| --- | --- |
| CAFFEINE | 17 mg |
| BENZOIC ACID* | 17 mg |
| EDTA · NA HYDRATE | 0.25 mg |

*or an equivalent concentration of sodium benzoate

Pilot Study

A confidential pilot study under the control of the Applicants established that nasal sprays containing therapeutically effective amounts of ascorbic acid and caffeine are effective in shortening the duration and relieving the symptoms of rhinitis.

Nasal spray formulations consisting essentially of ascorbic acid or sodium ascorbate in therapeutically effective amounts, benzoic acid or sodium benzoate, and disodium EDTA hydrate, produced relief of rhinitis symptoms within thirty minutes and decreased the duration of symptoms within forty-eight hours after beginning use of the spray. Relief from symptoms was achieved without significant side effects. The pilot study also showed that these nasal spray formulations shortened the duration of common cold symptoms from seven days to three days. Moreover, the formulations did not cause any rebound phenomenon of the nasal turbinates (Rhinitis Medicamentosa). Details of the pilot study are set forth below.

The pilot study was a double-blind, placebo-controlled trial of twelve persons (herein, subjects) presenting with an acute (less than 48 hours) flare-up of rhinitis symptoms (particularly, common cold symptoms) participated in the pilot study. After a detailed questionnaire was completed and signed by each subject, a careful history and physical examination were done of the ears, nose and throat and a nasal smear were taken. Each subject was given one of the nasal spray solutions shown in

TABLE III

NASAL SPRAY SOLUTIONS PREPARED IN ACCORDANCE WITH INVENTION[1]

| Equivalent Concentration of Ascorbic Acid | Sodium Ascorbate* Used (Concentration) | Caffeine Used (Concentration) | Benzoic Acid Used (Concentration) | EDTA.2Na Hydrate Used (Concentration) | Diluent (to final Volume of 150 ml) | Final pH after Adjustment with 20% NaOH** |
|---|---|---|---|---|---|---|
| 0 mg/ml | 0 g (0 mg/ml) | 2.55 g (17 mg/ml) | ***See below | 37.5 mg (0.25 mg/ml) | normal saline | 6.0 |
| 0 mg/ml | 0 g (0 mg/ml) | 0 g (0 mg/ml) | 0 g (0 mg/ml) | 0 mg (0 mg/ml) | normal saline | 7.4[2] |
| 250 mg/ml | 42.0 g (280 mg/ml) | 2.55 g (17 mg/ml) | 2.55 g (17 mg/ml) | 37.5 g (0.25 mg/ml) | deionized water | 6.0 |
| 300 mg/ml | 50.6 g (337 mg/ml) | 0 g (0 mg/ml) | 2.55 g (17 mg/ml) | 37.5 g (0.25 mg/ml) | deionized water | 5.5 |
| 375 mg/ml | 63.3 g (422 mg/ml) | 2.55 g (17 mg/ml) | 2.55 g (17 mg/ml) | 37.5 mg (0.25 mg/ml) | deionized water | 5.5 |

*Alternatively, ascorbic acid could be used directly by adding enough NaOH, NaHCO$_3$ or Na$_2$CO$_3$ to achieve the desired final pH.
**or sodium bicarbonate or sodium carbonate
***In this case, sodium benzoate was used instead of benzoic acid for solubility reasons. 3.0 g of sodium benzoate (20 mg/ml) was used, giving the equivalent of 17 mg/ml of benzoic acid in 150 ml of final solution. Sodium benzoate was also found to be useful in the preparation of the other solutions in this column.
[1]For each 10 ml of spray solution, 2 or 3 drops of Vi-Daylin multi-vitamin pediatric drops were added, so that all solutions had the same yellow color and had vitamin odor.
[2]No NaOH was added to the isotonic saline solution.

Table III containing either caffeine, caffeine plus ascorbic acid, or a placebo (isotonic salt water) in a tamper-proof, metered dose spray bottle. All nasal spray solutions were disguised to look and smell identical. Each subject was instructed to use one spray in each nostril every two hours while awake over a three-day period, until twenty (20) sprays per each nostril were administered. Each subject was re-examined on the third day to make sure the questionnaire was being completed correctly and that the nasal spray was being used as instructed. A second physical examination of the ears, nose and throat and a second nasal smear were obtained at that time. All subjects had to return the completed questionnaire within seven days after completing the study. The twelve subjects were randomized in a double-blind, placebo-controlled manner into the following five groups:

(1) Group A—ascorbic acid 375 mg/ml, caffeine 17 mg/ml, benzoic acid 17 mg/ml, EDTA. 2NA hydrate 0.25 mg/ml, deionized water to obtain a final solution of 150 ml, pH 5.5;

(2) Group B—ascorbic acid 250 mg/ml, caffeine 17 mg/ml, benzoic acid 17 mg/ml, EDTA.2NA hydrate 0.25 mg/ml, deionized water to obtain a final volume of 150 ml, pH 6.0;

Group C—ascorbic acid 300 mg/ml, benzoic acid 17 mg/ml, EDTA.2NA hydrate 0.25 mg/ml, deionized water to obtain a final volume of 150 ml, pH 5.5;

(4) Group D—caffeine 17 mg/ml, benzoic acid 17 mg/ml, EDTA- 2NA hydrate 0.25 mg/ml, normal saline used to reach a final volume of 150 ml, pH 6.0; and (5) Group E—normal isotonic saline at a pH of 7.4.

Three of the twelve subjects were randomly assigned to Group A. Two of these three subjects derived significant benefit from use of the nasal spray. One of these three subjects did not complete the protocol because she found the spray to be irritating to her nasal membranes; thus, she was eliminated from the final data.

Two subjects were randomly assigned to Group B. One of these two subjects found the spray to be significantly helpful, while the other subject found this particular nasal solution to be of no help.

Three subjects were randomly assigned to Group C. Two of these subjects found this nasal solution to be extremely beneficial. The third of these three subjects did not complete the pilot study requirements and was, thus, eliminated from the final data.

Two subjects were randomly assigned to Group D and both of these subjects found this solution to be extremely beneficial.

Two subjects were randomly assigned to Group E and neither of these subjects found this solution to be helpful.

In summary, twelve subjects participated in the pilot study, and two of the twelve subjects did not complete the protocol and were therefore eliminated from the final data (i.e. one subject from Group A and one subject from Group C). Of the ten subjects who did complete the study, seven of the eight subjects who used either ascorbic acid, or caffeine, or ascorbic acid plus caffeine found the nasal solutions to be effective. Only one subject using ascorbic acid (250 mg/ml) plus caffeine (17 mg/ml) did not find this nasal solution to be effective. The subjects who used normal saline were not helped by the placebo.

Preparation Of The Pharmaceutically Effective Solutions

The method of preparing each of the 150 ml solutions shown in Table III consisted of the following steps. One hundred milliliters (100 ml) of deionized water, or where noted, normal saline, was placed in a graduated 250 ml Erlenmeyer flask. Sodium ascorbate was added, and the mixture was swirled until the solid sodium ascorbate dissolved. Caffeine was added, followed by benzoic acid or an equivalent amount of sodium benzoate.

Alternatively, ascorbic acid rather than sodium ascorbate could be used, provided that sodium hydroxide, sodium bicarbonate, or sodium carbonate were used to adjust the final pH to the desired value.

For the solutions used in the pilot study which did not contain sodium ascorbate, benzoic acid was not soluble enough to achieve a concentration of 17 mg/ml. Instead of benzoic acid, 3.0 g of sodium benzoate (20 mg/ml) was used to give an equivalent of 17 ml/, equivalent to 17 mg/mL of benzoic acid) and ethylene diamine tetraacetic acid disodium salt hydrate were added.

The mixtures were diluted to about 140 ml and swirled (or magnetically stirred) until all of the solids dissolved. The pH of each solution was measured. If a pH was not between 5.5–6.0, the pH was adjusted with 20% sodium hydroxide (w/w solution) or with solid sodium bicarbonate or solid sodium carbonate to be within this range. The solutions were then diluted to the final volumes of 150 ml and transferred to brown glass Wheaton bottles. The bottles were labeled, capped, and stored in a refrigerator. It was noted that solutions prepared with the above method were stable and that the therapeutically effective amounts of ascorbic acid did not crystallize out of the solution.

Subsequent tests indicate that concentrations of Vitamin C of less than 200 mg/ml are therapeutically effective for treating acute and chronic rhinosinusitus and their symptoms. For treating acute rhinitis flare-ups, the novel composition can be administered every two hours for three days. Since the composition does not harm the nasal membranes, for treating chronic rhinosinusitis and its symptoms, the composition of the present invention can be administered indefinitely on an "as needed" basis.

It has been noted that other ingredients beyond those specifically set forth in Table III can be concurrently used with the composition. For example, other medications, pharmaceutically acceptable flavorants or odorants, other pharmaceutically acceptable buffering agents or preservatives, and the like, may additionally be utilized as needed and/or desired.

Those skilled in the art will appreciate from the foregoing description that the teachings of the present invention can be implemented in a variety of forms. Therefore, while certain preferred embodiments and features of the invention have been described above, the true scope of the invention should not be so limited since other modifications will become apparent to the skilled practitioner upon a study of the specification and the following claims.

We claim:

1. A stable, non-irritating aqueous nasal administered composition for treating the symptoms of acute or chronic rhinosinusitis and its associated upper airway symptoms consisting essentially of a therapeutically effective nasal spray having at least 20 mg per ml of Vitamin C; 5 to 100 mg per ml of caffeine; and a pharmaceutically acceptable aqueous carrier which is suitable for administering said Vitamin C and said caffeine to the nasal membrane of an individual afflicted with acute or chronic rhinosinusitis and wherein said carrier is optionally deionized water or normal saline solution, and wherein water soluble vitamins, at least one mineral, disodium EDTA hydrate and benzoic acid or sodium benzoate are optionally present.

2. The composition recited in claim 1 wherein said Vitamin C is supplied as sodium ascorbate or ascorbic acid.

3. The composition recited in claim 1 wherein said composition has a final pH of no greater than 6.5.

4. The composition recited in claim 1 wherein said pharmaceutically acceptable carrier is deionized water.

5. The composition recited in claim 1 wherein said pharmaceutically acceptable carrier is normal saline solution.

6. The composition recited in claim 4, wherein said mineral is selected from the group consisting essentially of zinc and selenium.

7. A stable, non-irritating aqueous nasal administered composition for treating the symptoms of rhinitis and its associated upper airway symptoms consisting essentially of a therapeutically effective nasal spray having at least 20 mg per ml of Vitamin C; at least 5 mg per ml of caffeine; and a pharmaceutically acceptable aqueous carrier which is suitable for administering said Vitamin C and said caffeine to the nasal membrane of an individual afflicted with acute or chronic rhinosinusitus, said composition having a final pH of 5.5 to 6.5 wherein any or a combination of water soluble vitamins selected from the group consisting of pantothenic acid, Vitamin B-6, Vitamin B-2, Vitamin B-1, Vitamin B-12, folic acid and at least one mineral, disodium EDTA hydrate, and benzoic acid or sodium benzoate are optionally present.

8. The composition recited in claim 7 wherein one or any combination of water soluble vitamins selected from the group consisting of pantothenic acid, Vitamin B-6, Vitamin B-2, Vitamin B-1, Vitamin B-12 and folic acid are present.

9. The composition recited in claim 7 wherein at least one mineral is present.

10. The composition recited in claim 7 wherein disodium EDTA hydrate and benzoic acid or sodium benzoate are present.

11. A stable, non-irritating nasal administered composition for treating the symptoms of acute and chronic rhinosinusitus and its associated upper airway symptoms consisting essentially of:

Vitamin C 20 to 200 mg/ml

Caffeine 5 to 100 mg/ml

Benzoic Acid about 17 mg/ml

EDTA about 0.25 mg/ml with the balance being a pharmaceutically acceptable aqueous carrier which is suitable for administering said Vitamin C and said caffeine to the nasal membrane of an individual afflicted with acute or chronic rhinosinusitus.

12. A product for treating the symptoms of acute and chronic rhinosinusitus and its associated upper airway symptoms consisting essentially of a stable, non-irritating aqueous composition containing 20 to 200 mg/ml of ascorbic acid and a pharmaceutically acceptable aqueous carrier; and a dispenser for administering said aqueous composition to a nasal membrane of an individual afflicted with acute or chronic rhinosinusitis.

13. A stable, non-irritating aqueous nasal administered stable composition for treating the symptoms of acute or chronic rhinosinusitis and its associated upper airway symptoms consisting essentially of a therapeutically effective nasal spray having at least 20 mg per ml of Vitamin C; caffeine; and a pharmaceutically acceptable carrier which is prepared by swirling a mixture of deionized water or normal saline, and sodium ascorbate until said sodium ascorbate is dissolved in said carrier; adding caffeine to said mixture of sodium ascorbate and said deionized water or normal saline; and adding benzoic acid or an equivalent amount of sodium benzoate.

14. A stable, non-irritating aqueous nasal administered stable composition for treating the symptoms of acute or chronic rhinosinusitis and its associated upper airway symptoms consisting essentially of a therapeutically effective nasal spray having at least 20 mg per ml of Vitamin C; caffeine; and a pharmaceutically acceptable carrier which is prepared by adding caffeine to a solution of deionized water or normal saline and ascorbic acid; and adding sodium hydroxide, sodium bicarbonate, or sodium carbonate to adjust the final pH to within 5.5 to 6.5.

15. A method for treating the symptoms of acute and chronic rhinosinusitus and its associated upper airway symptoms comprising the step of administering to the nasal membrane of an individual in need of such treatment a stable, non-irritating solution comprising at least 20 mg per ml of Vitamin C, 5 to 100 mg/ml of caffeine; and a pharmaceutically acceptable aqueous carrier which is suitable for administering said Vitamin C and said caffeine to the nasal membrane of an individual afflicted with acute or chronic rhinosinusitus and wherein said carrier is optionally deionized water or normal saline solution, and wherein one or any combination of vitamins selected from the group consisting of pantothenic acid, Vitamin B-6, Vitamin B-2, Vitamin B-1, Vitamin B-12 and folic acid, and one mineral are optionally present in said solution.

16. The method recited in claim 15 wherein said solution has a pH of no greater than 6.5.

17. The method recited in claim 15 wherein said solution is administered to the nasal membrane as a nasal spray.

18. The method recited in claim 15 wherein said solution is administered to the nasal membrane as drops topically applied to the nasal turbinates.

19. The method recited in claim 15 wherein said solution is administered for treating the symptoms of acute and chronic rhinosinusitus and its associated airway symptoms to the nasal membrane of said individual about every two hours for about three days.

20. The method recited in claim 15 wherein one or any combination of vitamins selected from the group consisting of pantothenic acid, Vitamin B-6, Vitamin B-2, Vitamin B-1, Vitamin B-12 and folic acid is in said solution.

21. The method recited in claim 15 wherein at least one mineral is dissolved in said solution.

22. The method recited in claim 15 wherein said pharmaceutically acceptable carrier is deionized water.

* * * * *

Disclaimer 5,508,282 - Jeffrey Tulin-Silver; William H. Pearson, both of Ann Arbor, Michigan. COMPOSITION AND METHOD FOR TREATING ACUTE OR CHRONIC RHINOSINUSITIS. Patent dated April 16, 1996. Disclaimer filed September 30, 1999, by the assignee, Jeffrey Tulin-Silver.

Hereby enters this disclaimer to claim 12 of said patent.

*(Official Gazette,* December 28, 1999)

(12) REEXAMINATION CERTIFICATE (4257th)
United States Patent
Tulin-Silver et al.

(10) Number: US 5,508,282 C1
(45) Certificate Issued: *Jan. 23, 2001

(54) COMPOSITION AND METHOD FOR TREATING ACUTE OR CHRONIC RHINOSINUSITIS

(75) Inventors: Jeffrey Tulin-Silver, 2818 Parkridge, Ann Arbor, MI (US) 48103; William H. Pearson, Ann Arbor, MI (US)

(73) Assignee: Jeffrey Tulin-Silver, Ann Arbor, MI (US)

Reexamination Request:
No. 90/005,536, Oct. 21, 1999

Reexamination Certificate for:
Patent No.: 5,508,282
Issued: Apr. 16, 1996
Appl. No.: 08/061,548
Filed: May 17, 1993

(*) Notice: This patent is subject to a terminal disclaimer.

(51) Int. Cl.$^7$ .......................... A61K 31/52; A61K 31/34
(52) U.S. Cl. ............................................. 514/264; 514/474
(58) Field of Search ..................................... 514/474, 264

(56) References Cited

PUBLICATIONS

Declaration of Jeffrey Tulin–Silver, M.D. and Exhibit 1: Ocean, Nasal spray label, Fleming & Co., Fenton, MO 63026; and Exhibit 2: Fleming Newsletter copy (no date available).

Gotzsche, A.L., "Pernasal Vitamin C and the Common Cold", *The Lancet*, 2:1039 (Oct. 28, 1989).

The Merck Index, 11$^{th}$ Ed., p. 247 (1989).

The Merck Index, 11$^{th}$ Ed., p. 248 (1989).

Podoshin, L, et al., "Treatment of Perennial Allergic Rhinitis with Ascorbic Acid Solution," Letters to the Editor, *ENT Journal*, 70(1):54–55 (1991).

Rogawski, M. et al., "Cafaminol in the Treatment of Acute Rhinitis," *Wiad–Lek*, 38(20):1437–1439 (Oct. 15, 1985) (English Abstract Only).

Shapiro, Philip, "Caffeine for Allergic Rhinitis," *The Lancet*, 1(8275):793 (Apr. 3, 1982).

*Primary Examiner*—Ray Henley, III

(57) ABSTRACT

A stable, non-irritating composition and method for treating, without side effects, acute or chronic rhinosinusitis and its associated upper airway symptoms. The composition and treatment are useful for relieving the symptons, and shortening the duration, of acute or chronic rhinosinusitis. The composition comprises a therapeutically effective solution having a pH of about 6.0, of ascorbic acid and caffeine, in combination with other soluble vitamins, natural ingredients and preservatives in a pharmaceutically acceptable carrier. The method includes the steps of preparing and administering the composition to the nasal membranes of a patient in the form of a nasal spray or drops.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–11 and 13–22 is confirmed.

Claim 12 was previously disclaimed.

* * * * *